United States Patent [19]

Kosti

[11] 4,348,378

[45] Sep. 7, 1982

[54] PLAQUE DISCLOSING DENTIFRICE COMPOSITIONS WITH SEMI-SOLID MICROCAPSULES OF DYE

[76] Inventor: Carl M. Kosti, 704 Foxhall Rd., Bloomfield Hills, Mich. 48013

[21] Appl. No.: 194,921

[22] Filed: Oct. 7, 1980

Related U.S. Application Data

[63] Continuation-in-part of Ser. No. 65,078, Aug. 9, 1979, abandoned.

[51] Int. Cl.³ .......................... A61K 7/16; A61K 7/18
[52] U.S. Cl. .......................................... 424/7; 424/49; 424/52; 424/57
[58] Field of Search .................. 424/7, 49–58

[56] References Cited

U.S. PATENT DOCUMENTS

| | | | |
|---|---|---|---|
| Re. 29,634 | 5/1978 | Roberts et al. | 424/49 |
| 1,484,415 | 2/1924 | Shepherd | 424/49 |
| 1,645,791 | 10/1927 | Brownlee | 424/49 |
| 1,933,977 | 11/1933 | Harris | 424/49 |
| 2,024,146 | 12/1935 | Crowther | 424/49 |
| 2,031,233 | 2/1936 | Stillwall | 424/49 |
| 2,216,485 | 10/1940 | Brandt | 424/49 |
| 2,325,421 | 7/1943 | Omohundro et al. | 424/7 |
| 2,658,851 | 11/1953 | Brandenberger | 424/49 |
| 2,988,483 | 6/1961 | Barsky et al. | 424/49 |
| 2,994,642 | 8/1961 | Bossard | 424/49 |
| 3,309,274 | 3/1967 | Brilliant | 424/7 |
| 3,609,102 | 9/1971 | Schlossman | 424/7 |
| 3,705,940 | 12/1972 | Kirchgassner | 424/49 |
| 3,723,613 | 3/1973 | Block et al. | 424/7 |
| 3,903,252 | 9/1975 | Stearns et al. | 424/7 |
| 3,919,409 | 11/1975 | Perla et al. | 424/49 |
| 4,067,840 | 1/1978 | Wolf | 260/29.6 R |
| 4,069,311 | 1/1978 | Mannara | 424/49 |
| 4,071,614 | 1/1978 | Grimm | 424/7 |
| 4,089,943 | 5/1978 | Roberts et al. | 424/49 |
| 4,196,189 | 4/1980 | Raaf et al. | 424/49 |
| 4,202,878 | 5/1980 | Ritze | 424/7 |

FOREIGN PATENT DOCUMENTS

| | | |
|---|---|---|
| 2104473 | 8/1972 | Fed. Rep. of Germany . |
| 2238332 | 2/1974 | Fed. Rep. of Germany . |
| 2416272 | 10/1975 | Fed. Rep. of Germany . |
| 2002622 | 7/1976 | Fed. Rep. of Germany . |
| 2203618 | 5/1974 | France . |
| 2242968 | 4/1976 | France . |
| 1268635 | 3/1972 | United Kingdom . |

*Primary Examiner*—Shep K. Rose
*Attorney, Agent, or Firm*—Gifford, VanOphem, Sheridan & Sprinkle

[57] ABSTRACT

This invention relates to novel plaque disclosing compositions for use in the self-evaluation and motivation of oral hygiene practices. Still, more particularly, the invention relates to incorporated water insoluble, water immiscible, pressure rupturable, dispersed, emulsed particles and capsules containing a plaque disclosing dye element in toothpaste compositions.

21 Claims, No Drawings

PLAQUE DISCLOSING DENTIFRICE COMPOSITIONS WITH SEMI-SOLID MICROCAPSULES OF DYE

CROSS REFERENCE

This is a continuation-in-part of my copending U.S. Patent Application Ser. No. 065,078 filed Aug. 9, 1979 now abandoned. That application is hereby incorporated by reference and made a part hereof, and benefit of its filing date is claimed.

BACKGROUND OF THE INVENTION

I. Field of the Invention

The destruction of teeth by dental caries and the loss of their support through inflammatory periodontal disease is related to the activity of microbial plaque. Although differing in particulars, the relationships are essentially identical: pathogenic microorganisms become attached to a tooth, take in nutrients and liberate chemicals that are injurious to the target site, whether tooth, periodontium, or both. The attachment of organisms can be effected by growth in the sheltered areas such as the pits, fissures and faults of teeth, by self-produced adherence and colonization, such as in plaque formation, or by a combination of processes. Given sufficient nutrients and time to form toxic substances, the microorganisms will produce carious and periodontal lesions at susceptible sites.

II. Description of the Prior Art

The problem of preventing caries and inflammatory periodontal disease has been approached experimentally by attempting to interfere with plaque formation and activity and by altering tooth surfaces. Attempts to change the surface characteristics of teeth to prevent the colonization of microorganisms have not been successful. Alterations in the chemical rather than physical characteristics of the target site have been achieved to some extent by the exposure of the tooth surfaces to fluoride ions made available in water supply, dietary preparations, dentifrices, mouthwashes, topically applied solutions and gels, and respective materials. Unfortunately, no such simple and effective agent is available to alter the soft tissues. The most successful control of plaque related to periodontal disease has been professional mechanical removal.

In rather general terms, dental plaque has been described as a tenacious, soft deposit consisting chiefly of bacteria and bacterial products. Dental plaque forms on tooth surfaces, restorations, appliances, and dentures. More precisely, plaque includes specific types of bacterial colonies surrounded by gel-like intercellular substances derived chiefly from the bacteria themselves, but also containing components from saliva and crevicular fluid, leucocytes and epithelial cells. The microflora of the plaque is water insoluble and must be mechanically removed. Oral water irrigators, whether of the pulsating or steady stream type, are considered as adjuncts to the toothbrush in helping to maintain oral health but plaque being water insoluble, is not significantly removed from the tooth sites.

The brushing of the teeth and gingiva has been the home care procedure most widely recommended to promote oral cleanliness. Its basic purpose is to remove oral accumulations of plaque and debris and thereby assist in the prevention of dental disease, particularly when used with an appropriately fluoride containing, abrasive dentifrice. However, the thorough removal of dental plaque by home care procedures can be taught more easily if the plaque can actually be seen. A number of agents and techniques have been developed, some of which may be used conveniently and economically at home, whereas others may be used more effectively by the dentist at the time of instruction. The disclosing agent, erythrosine (FD&C Red. No. 3), is probably the agent most frequently employed for use in the home. It has an aesthetic advantage of being a color similar to that of oral soft tissues, but it does have the disadvantage of staining any epithelial tissues, such as lips, tongue, fingers and other materials it may come in contact with, particularly cloth and sink areas. This indiscriminate staining is due to the water solubility of erythrosine and the like vegetable and organic dye products. A mixture of two dyes, again water soluble, FD & C Green No. 3 and FD & C Red No. 3, has been used and plaque appears to be differentially stained depending on age or thickness—the thicker plaque staining blue and the thinner, red. An agent such as this would be helpful in demonstrating to the patient those sites most frequently missed in cleansing procedures. Still another procedure using a colorless agent has been suggested for plaque visualization. Solutions of sodium fluorescein are essentially colorless by visible light but fluoresce strongly in light having a wave length of approximately 4800 A°. Again, this procedure would necessitate special lighting equipment and is time consuming as well as economically costly.

The composition of the plaque moreover, appears to be lipoidal in nature and the interfacial tension between an aqueous dye solution or composition and the lipid is quite high. Conventional staining formulations wherein the dye is dissolved directly in water, therefore, have employed a relatively large amount of dye to circumvent this interfacial tension. As a result, excess staining of the entire oral cavity as well as non-oral objects normally results when these formulations with large dye percentages are used.

SUMMARY OF THE INVENTION

The present invention obviates these and other problems of the prior art by providing disclosing compositions in water insoluble medium containing a dye which is quickly and selectively adsorbable by plaque formation in the oral cavity. This relatively quick selective adsorption by the dental plaque formations of the water insoluble, water immiscible phase containing the dye element of the invention circumvents the length of time necessary for contact of the present compositions with tooth surfaces, preventing aestehtically unacceptable staining of the mucous membranes of the oral cavity and non-oral objects.

It is, therefore, the primary object of the present invention to provide an improved plaque disclosing compositions for use in the oral cavity in the self evaluation and motivation of oral hygiene practices.

It is another object of the present invention to provide improved plaque disclosing compositions which selectively identify areas of plaque formation on tooth surfaces without appreciably staining other portions of the oral cavity and non-oral objects.

It is yet another object of the present invention to provide plaque disclosing compositions of the type stated comprising a water insoluble, water immiscible, hydrophobic phase dispersed and otherwise emulsed in a water soluble, water miscible, hydrophilic phase.

It is a further object of the present invention to provide plaque disclosing compositions of the type stated wherein the water insoluble, water immiscible, hydrophobic phase comprises the plaque disclosing dye element emulsed in fine droplets or encapsulated in pressure rupturable capsules, and wherein the water soluble, water miscible, hydrophilic phase comprises the sweeteners, flavoring agents, abrasives, humectants, thickening and emulsifying agents, fluorides, preservatives, and water, the two phases being in an intimate combination which, when applied to the teeth in the oral cavity, will not appreciably stain areas free of plaque formations, the excess being readily removed by rinsing with water and other rinsing solutions.

It is still another object of the present invention to provide plaque disclosing compositions of the type stated which when applied topically to the tooth surfaces and then mechanically or manually agitated with an object, such as a toothbrush, in a fluid medium, such as the saliva, would rupture the capsule or remove the protective core surrounding each particle of the dye element from the water insoluble, water immiscible, hydrophobic medium and liberate the said dye element on the plaque surfaces where, being dissolved by the action of the saliva, would render the plaque formation visually distinguishable from the enamel and other portions of the oral cavity.

It is an additional object of the present invention to provide plaque disclosing compositions of the type stated where the water insoluble, water immiscible, hydrophobic phase containing the dye element therein, is preferably soft, semi-solid, or soft-solid state eliminating the undesirable relative free flow of the dye element as is the common characteristic of fluid plaque disclosing preparations.

It is also an object of the present invention to provide plaque disclosing compositions of the type stated and a method and a process of making such compositions comprising a phase of water insoluble, water immiscible, hydrophobic substance suspended, dispersed or emulsed in a second phase of water soluble, water miscible, hydrophilic substance, the former comprising disclosing dye elements and the latter having the pharmaceutical and physical aids which can be mass produced inexpensively, efficiently, and simply. Other objects and advantages of the present invention will be apparent to those skilled in the art on reading the following disclosure, and therefore, the invention includes the new and novel compositions and processes of making and using the compositions herein illustrated.

The invention deals with plaque disclosing compositions in gel or paste form for topical application in the oral cavity for selectively staining the sites of dental plaque formations comprising:

(1) a continuous phase of water soluble, water miscible, hydrophilic colloid containing pharmacological and physical aids such as sweeteners, flavoring agents, humectants, abrasives, thickeners and emulsifiers, fluorides, preservatives, alcohols, non-staining coloring agents, and water, and uniformly dispersed throughout said continuous phase;

(2) a discontinuous phase of plaque disclosing dye elements each comprising a coating or protective covering consisting of:
 (a) a soft semi-solid or solid water insoluble, water immiscible, hydrophobic fine droplet of the emulsified plaque staining dye element, or
 (b) a soft, semi-solid, or solid water insoluble, water immiscible, hydrophobic pressure rupturable capsule of the emulsified plaque staining dye elements.

The dye elements are rendered substantially less water soluble when effectively applied in the oral cavity permitting selective adsorption and then absorption by any plaque sites in the oral cavity, of the plaque disclosing dye elements when pressure is applied on said plaque disclosing compositions rupturing the dye containing droplets or capsules liberating the now water soluble dye element, without appreciably staining other parts of the oral cavity and non-oral objects, the excess of the plaque disclosing compositions being readily removed by rinsing with water and other rinsing solutions.

The term "hydrophobic" is a general descriptive adjective for a group of organic substances of fatty nature which are water insoluble and water immiscible but soluble in fat solvents.

The term "hydrophilic" is a general descriptive adjective for a group of organic and inorganic substances which naturally form colloidal suspensions when mixed with water but are usually not soluble in fat solvents.

The term "absorption" is a general descriptive word referring to passage of water and dissolved substances into cells.

The term "adsorption" in the context of the present invention refers to adherence of atoms, molecules, or ions of any kind to the surface of a solid or semi-solid.

The term "dispersion" is a system of minute particles distinct and separate from one another and suspended in a medium. A "suspension" is a two-phase system consisting of a finely divided solid or semi-solid dispersed in another solid or in a fluid. An "emulsion" is an intimate mixture of two immiscible liquids (such as oil and water) in which one of the liquids is in the form of fine droplets is dispersed in the other.

The present invention is directed toward improved plaque disclosing compositions and the process of making them efficiently and inexpensively in gel or paste form for topical administration to the teeth and as a diagnostic measure for self evaluation of the tooth brushing habits when the plaque formations are rendered visible to the naked eye. The compositions of the present invention include physiologically and pharmacologically harmless dyes suspended in equally physiologically and pharmacologically harmless water insoluble, water immiscible, hydrophobic substances which have high affinity for adsorption by the dental plaque formations without appreciably affecting the other parts of the oral cavity and non-oral objects. Moreover, the inherent attractive forces operating from the water insoluble substances to the lipid dental plaque matrix composition with unbalanced forces of attraction between the two systems allow for a significantly lower concentration of the dye to be employed in a selective manner than is possible in an aqueous dye solution where the interfacial tension between the free moving dye elements and the lipid dental plaque composition is quite high.

Conventional liquid staining solutions, therefore, have employed a relatively large amount of dye to circumvent this interfacial tension. As a result, excess staining of the entire oral cavity, as well as non-oral objects, normally results when these aqueous solutions are used. Furthermore, in the present invention, the water insoluble substance forms a protective but adsorbable film over each dye particle rendering the dye potentially less water soluble and easily removable from the oral cavity by rinsing with water without appreciably affecting the adsorbed dye on the surface of the plaque formation. The attractive forces of adhesion between the semi-solid water insoluble protective coating and the lipid dental plaque formation renders the plaque readily visible to the naked eye and can best be removed by tooth-brushing of the stained plaque.

The water insoluble phase of the subject disclosing compositions acts locally when applied to the dental plaque in physical and chemical manner. As described above, there exist molecular and electromotive attractive forces between the water insoluble protective film wherein the dye element is suspended, and the dental plaque. This physical attraction confines the dye to the site of plaque formation without undesirably staining the other parts of the oral cavity. Chemically, then, when a toothbrush is applied to the site of dye accumulation, the water insoluble emulsed droplets and capsules containing the dye element will rupture liberating the water soluble dye element to be dissolved in the saliva and be absorbed by the dental plaque rendering so affected plaque distinguishable from the other parts of the tooth structure surface.

The plaque disclosing compositions of the present invention are best made by dispersing a selected amount of the physiologically and pharmacologically harmless dye in an equally physiologically and pharmacologically harmless selected water insoluble, water immiscible, hydrophobic substances, incorporating a selected amount of such water insoluble phase in a water soluble colloidal phase wherein dissolved are the flavoring agents, sweeteners, abrasives, humectants, thickening and emulsifying agents, fluorides, preservatives and other pharmaceutical and physical aids and intimately mixing the two systems until a homogeneous emulsion is obtained. This water soluble colloidal phase may, of course, be a conventional toothpaste. It has been found for best results that the water soluble phase of the present plaque disclosing compositions should not be less than twice the amount of water insoluble phase (2:1).

Furthermore, in addition to the plaque disclosing dye element the water insoluble, water immiscible, hydrophobic phase may contain incorporated therein the pharmacological and physical aids, such as sweeteners, flavoring agents, abrasives, humectants, thickeners and emulsifiers, fluorides, etc., in part or in total, in selected amounts without materially altering the scope and the intent of the present invention. However, most aids being water soluble are best utilized when dissolved in water resulting in better plaque disclosing compositions with more acceptable consistencies. In essence, only thickening and emulsifying agents must be present in the water phase of the present invention when emulsified with the water insoluble phase.

The disclosing compositions of the present invention are effectively used by topically applying the same to the teeth allowing for selective absorption and staining of plaque formation in the oral cavity rendering the plaque readily visible with the naked eye. The stained plaque site will not be removed during the initial rinsing process; the excess amount of the disclosing composition may easily be removed by rinsing with water or other rinsing solutions.

DESCRIPTION OF THE PREFERRED EMBODIMENT

The plaque disclosing compositions of the present invention are found to be highly effective in selectively staining the sites of plaque formations in the oral cavity through topical application to the teeth clearly distinguishing the plaque formation from the rest of the oral cavity. The excess of the composition is readily removed by rinsing with water without affecting the dye which is absorbed by the dental plaque that can only be removed by subsequent toothbrushing.

The dispersing medium, of course, must be selected from those that are physiologically and chemically tolerable with reference to the particular oral utility of the invention and must be water insoluble. It may either be semi-solid or solid and will disperse or microencapsulate the dye. It has been found in connection with the present invention that the most suitable water insoluble media for dye dispersion are:

(1) Lipids
  (a) Simple Lipids—esters of fatty acids with various alcohols
    i. Fats—esters of fatty acids with glycerol. Lanolin; Anhydrous lanolin.
    ii. Waxes—esters of fatty acids with alcohols other than glycerol. White wax; yellow wax.
  (b) Compound Lipids—esters of fatty acids containing groups in addition to an alcohol and the fatty acid.
  (c) Derived Lipids—substances derived from the above groups by hydrolysis.
    i. Fatty acids, both saturated and unsaturated.
    ii. Glycerols.
    iii. Sterols and other steroids.
    iv. Alcohols other than glycerol and sterols.
    V. Fatty aldehydes.
(2) Alkane Series Hydrocarbons. They are substances derived from petroleum by distillation, chilling, chemical purification and filtration, consisting of hydrocarbons of methane and related series, and not subject to hydrolysis. Mineral oil; petrolatum; white petrolatum; paraffin.
(3) Fixed Oils. Neutral esters of vegetable derivation, being compounds of acids (chiefly lauric, oleic, palmitic and stearic) with glycerin. Cottonseed oil; olive oil.
(4) Resins. Substances derived from plant origin. Canada balsam; Peruvian balsam; copal; mastic; rosin; benzoin.

The insoluble substance selected for use in the compositions of the present invention for dye dispersion is preferably an alkane oil of the general formula $C_nH_{2n+2}$. This substance is commercially available and chemically known as "Petrolatum", a pharmacologically innocuous, practically odorless and tasteless, soft semisolid which is insoluble in water and practically insoluble in glycerol and alcohol. I have found that this substance is highly effective in subject disclosing compositions and can be incorporated in various proportions to the total volume of the disclosing compositions while remaining relatively free for adsorption by the plaque formations without appreciably staining the other parts of the oral cavity and non-oral objects. Nevertheless, the excess is easily removed by rinsing with water. The soft semisolid consistency of the selected substance prevents free migration of the encapsulated and dispersed dyestuff and is readily emulsified with the water soluble phase of the plaque disclosing compositions. For the most effective results, the water insoluble substance is present in an operative range in an amount from about 0.1 percent to about 50 percent by weight with respect to the total weight of the composition and preferably present in an operative range of about 1 percent to about 35 percent by weight with respect to the weight of the total composition, the balance being a dye and the water soluble base consisting of sweetening agents, flavoring agents, abrasives, thickening and binding agents, moisture retaining agents, preservatives, fluorides, water, and other pharmaceutical, physical and mechanical aids in desired amounts.

The disclosing compositions produced in accordance with the present invention and which use the solid microencapsulation method for making such compositions are physiologically and pharmacologically innocuous polymers and copolymers such as polymerizing acrylonitrile; butadiene and styrene monomers; acetal copolymers; acetal homopolymers; acrylics; allyls; aminos; cellulosics; epoxys; fluoroplastics; furans; ionomers; nitrile barrier resins; nylons; phenolics; phenylene-oxide based resins; poly(amide-imide); polyaryl ethers; polyaryl sulfones; polybutadienes; polybutylenes; polycarbonates; polyesters; polyethersulfones; polyethylenes; polyimides; polyphenylene sulfides; polypropylenes; polystyrenes; polysulfones; polyurethanes; polyvinyls; silicones; salts of heavy metals cellulose sulfates; other water soluble materials such as gelatin and gelatin derivatives of which gelatin is the main radical; colloidal albumen; hydrolysed polyvinyl acetate; hydrolysed cellulose esters such as cellulose acetate hydrolysed to an acetyl content of 19 to 26 percent; polyacrylamide or an imidized polyacrylamide; polyvinyl alcohol; a vinyl alcohol polymer containing urethane carboxylic acid groups such as the vinyl alcohol-cyanoacetate vinyl copolymer; or a polymer material which results from polymerizing protein with a monomer having a vinyl group; polyethylene oxide; naturally occuring or synehetic alginates such as salts of water soluble heavy metals of sodium, potassium and magnesium, and any combination or mixture thereof.

The most suitable members of these classes used in accordance with the present invention in making the solid microencapsulation method of the disclosing compositions comprise preferably tributyl phosphate; poly(-vinyl methylether/maleic anhydride) copolymer half amide, ammonium salt; polyethylene oxide; ethylenemaleic anhydride copolymer, half ethyl ether, containing concentrated ammonia. The concentration of the microencapsulating material for the most effective result of the present disclosing compositions is present in operative range in an amount from about 0.1 percent to about 50 percent by weight with respect to the weight of total composition and preferably present in an operative range of about 1 percent to about 35 percent by weight with respect to the total weight of the composition, the balance being (1) a dye and (2) the water soluble base comprising sweetening agents, flavoring agents, abrasives, thickening and binding agents, moisture retaining agents, preservatives, fluorides, water, and other pharmaceutical, physical and mechanical aids in desired amounts.

In addition, in accordance with the present invention, the components specified herein will generally have additives performing specific desired functions such as coating agents, hardeners, plasticizers, viscosity increasing agents, stabilizers, preservatives, dissolution speed-increasing agents, pH altering substances to maintain the pH at about 4 to 12 and other manufacturing addendas.

The disclosing compositions produced in accordance with the present invention consist of coloring agents that are pharmacologically and physiologically nontoxic when used in suggested amounts, the said coloring agents comprise a member of a group consisting of substances which are dyes, pigments or other substances made by a process, of synthesis or similar artifice, extracted, isolated, or otherwise derived, with or without intermediate or final change of identity, from a vegetable, animal, mineral, or other source that, when added or applied to plaque formation or any other surface or substance, is capable, alone or through reaction with other substance, of imparting a color thereto. Some examples of the members of the group are azo dyes, acridine dyes, fluorescein (pyronine) dyes, phenolphthalein dyes, triphenylmethane (rosaniline) dyes, and methylene blue.

The most advantageous dyes for use in the plaque disclosing compositions of the present invention are food color additives that are presently certified under the Food, Drug & Cosmetic Act for use in food and ingested drugs, including dyes such as FD&C Red No. 3 (sodium salt of tetraiodofluorescein), FD&C Yellow No. 5 (sodium salt of 4-p-sulfophenylazo-1-p-sulfophenyl-5-hydroxypyrazole-3-carboxylic acid), FD&C Yellow No. 6 (sodium salt of p-sulfophenylazo-$\beta$-naphtol-6-monosulfonate), FD&C Green No. 3 (disodium salt of 4-{[4-(N-ethyl-p-sulfobenzylamino)-phenyl]-(4-hydroxy-2-sulfoniumphenyl)-methylene}-[1-(N-ethyl-N-p-sulfobenzyl)-$\Delta$-3,5-cyclohexadienimine], FD&C Blue No. 1 (disodium salt of dibenzyldiethyl-diaminotriphenylcarbinol trisulfonic acid anhydrite), FD&C Blue No. 2 (sodium salt of disulfonic acid of indigotin) and mixtures thereof in various proprotions. The concentration of the dye for the most effective result in the present invention is present in the operative range in an amount from about 0.05 percent to about 25 percent by weight with respect to the weight of the total composition and preferably present from about 0.1 percent to about 10 percent of the total weight of the composition.

It has been found that any of the above dyes are very effective in the context of the present disclosing compositions in that they can be incorporated in water insoluble medium without dissolution and still remain relatively free for adsorption and absorption by plaque formation in the oral cavity. The water insoluble substance coats and thus encapsulates each individual dye particle and being soft semisolid, tenaciously hangs on to the dye and, therefore, prevents substantial undesired discoloration of the other parts of the oral cavity and non-oral objects.

Each of the aforementioned components, namely the dye and the water insoluble phase (medium) is suspended and emulsed in water soluble medium composed of a thickening and binding agent in water. The thickening and binding agent is preferably an emulsifying substance which is added to the composition in a nontoxic amount and is pharmacologically compatible with the water insoluble phase to form finely divided water insoluble particles containing the dye when the two phases are mixed. However, the amount must be sufficient to provide a composition thick enough to permit topical application to the oral cavity without free flowing effect and subsequent undesired staining of other parts of the oral cavity and non-oral objects. Some of the preferred substances that meet the requirements of the present plaque disclosing compositions are mucilaginous substances selected from the group consisting of acacia; bentonite; carrageenan-Irish moss extractive of sodium, potassium or calcium salt; methylcellulose; sodium carboxymethycellulose; sterculia gum; tragacanth; sodium, pottasium and magnesium alginates; polyethylene glycols; gelatin; guar gum; xanthan gum; propylene glycol alginates; galactomannans and like substances, and mixtures thereof. The concentration of the thickening and emulsifying agent which may be used in the compositions of the present invention is present in the amount from about 0.05 percent to about 10 percent by weight with respect to the weight of the total weight of the composition and preferably present from about 0.1 to about 5 percent of the total weight of the composition.

The compositions of the present invention may also include flavoring agents, sweeteners, abrasives, moisture retaining substances, fluorides, preservatives and alcohols, and foaming and surface active agents.

Some of the sweetening agents that can be used in the subject disclosing compositions are selected from the group consisting of saccharine, sodium saccharine, xylitol, sorbitol, sodium cyclamate and sugar, and mixtures thereof.

Examples of abrasives are calcium carbonate, one or more of the calcium phosphates, calcium sulfate, hydrated aluminum oxide, magnesium carbonate and phosphate, sodium bicarbonate, dibasic and tribasic sodium phosphate, hydrated silica xerogel, hydrated silica aerogel, magnesium oxide, insoluble sodium metaphosphate, anhydrous dicalcium phosphate, and mixtures thereof.

Examples of moisture retaining substances or humectants are glycerin, propylene glycol, polyethylene glycol in the series from 10 and up, but not limited to 50,000, diethylene glycol monoethyl ether, sorbitol, polysorbate, polyethylene sorbitan monolaurate, polyoxyethylene sorbitan monolaurate, (etc.) and mixtures thereof.

Examples of foaming and surface active agents that can be used in the disclosing compositions of the present invention are dioctyl sodium sulfosuccinate, sodium alkyl sulfoacetate, sodium lauryl sulfate, sulfocolaurate, sodium lauryl sarcocinate, sodium coconut monoglycerite sulfonate, benzalkonium chloride, benzelthonium chloride, thonzonium bromide, cetyl pyridinium bromide, cetyl pyridinium chloride, sodium tetradecyl sulfate, (etc.) and mixtures thereof.

Examples of flavoring agents which can be used in the disclosing compositions of the present invention are essential oils such as anise oil, cinnamon oil, clove oil, eucalyptol, eucalyptus oil, eugenol, menthol, methyl salycilate, peppermint oil, spearmint oil, natural or synthetic substances such as blackberry, strawberry, cherry, grape, lime, lemon, mint, (etc.) and mixtures thereof.

Examples of fluorides are sodium fluoride, stannous fluoride, sodium monofluorophosphate, (etc.) and mixtures thereof.

Examples of preservatives which can be used in the disclosing compositions of the present invention are methylparaben, propylparaben, phenylmercuric nitrate, sodium bisulfite, sodium nitrite, sodium thiosulfate, sodium benzoate, ethylenediaminetetraacetic acid, chlorobutanol, thimerosal, phenylmercuric acetate, disodium calcium EDTA, (etc.) and mixtures thereof.

The compositions of the present invention may also include certain alcohols and water.

The disclosing compositions produced in accordance with the present invention will generally have components specified herein in the amounts of from about 0.05 percent to about 5 percent sweetening agent; from about 0.05 percent to about 25 percent flavoring agents; from about 2.0 percent to about 65 percent humectants; from about 0.05 percent to about 5.0 percent surfactants; from about 0.05 percent to about 10.0 percent mucilaginous agents; from about 0.10 percent to about 5.0 percent fluoride compounds; from about 1.0 percent to about 65 percent abrasive agents; from about 0.10 percent to about 20 percent alcohols, from about 0.05 percent to about 5.0 percent preservative; from about 0.0001 percent to about 5.0 percent of an added coloring agent; and from about 0.0 percent to about 50.0 percent water.

The concentration of the water soluble, water miscible, hydrophilic phase is dependent upon the consistency desired and may be present in the operative range in an amount from about 0.5 percent to about 75 percent by weight with respect to the weight of total composition and preferably present in an operative range of about 5 percent to about 65 percent by weight with respect to the total weight of the composition.

In summary, the plaque disclosing compositions of the present invention comprise a dyestuff and encapsulated by a water insoluble, solid or semi-solid substance and a water soluble colloidal phase comprising pharmacological and physical aids such as sweetening agents, abrasives, humectants, fluorides, alcohols, preservatives, etc. all or in part. The two immiscible phases are mechanically mixed into an intimate emulsion in such a way that the water insoluble phase containing the dyestuff is dispersed in the form of fine droplets in the water soluble phase with the aid of an emulsifier and a mechanical shear device such as a colloidal mill. The dye component is rendered substantially less water soluble when effectively applied to the oral cavity, permitting selective adsorption and absorption by any plaque containing site in the oral cavity, the excess amounts of the plaque disclosing compositions being easily rinsed from the oral cavity by tap water and other rinsing solutions without undesirably staining other portions of the oral cavity and non-oral objects. The adsorbed dye by the attractive forces of adhesion existing between the water insoluble protective covering and the plaque matrix first tenaciously attached to the surface of the plaque formation and subsequently is effectively wiped off from its water insoluble film by the mechanical action of the toothbrush, subsequently becoming dissolved by the action of the saliva, rendering the plaque readily visible to the naked eye. The stained plaque formation may then be removed in a subsequent toothbrushing procedure.

Furthermore, the pharmacological and physical aids may, in part or in whole, in selected amounts, be incorporated in the water insoluble phase containing the dye without materially altering the scope of the present invention. However, most aids being water soluble are best utilized when dissolved in water resulting in better plaque disclosing compositions with more acceptable consistencies. Only a thickening and emulsifying agent need be present in the water phase of the present invention when emulsified with the water insoluble phase.

EXAMPLES

In order to point out more fully the nature of the present invention, the following specific examples are given as an illustrative embodiment of the present process and compositions produced thereby.

EXAMPLE 1

(A) In 100 grams Petrolatum, 4 grams of Erythrosine (FD&C Red No. 3) is suspended and run through a colloidal mill three times to obtain a homogeneous suspension.

(B) The water soluble phase contains the following:

|  | Weight % |
| --- | --- |
| Sodium monofluorophosphate | 0.76 |
| Calcium carbonate | 12.60 |
| Silica | 12.00 |
| Sorbitol (70% solution) | 52.80 |
| Polyethylene glycol | 3.00 |
| Sodium lauryl sulfate | 1.15 |
| Water | 15.00 |
| Sodium carboxymethylcellulose | 1.50 |
| Peppermint Oil | 1.00 |
| Methylparaben | 0.19 |

After the water insoluble, semi-solid dye suspension (A) has been prepared to desired consistency, 10 grams of this composition is slowly added to 100 grams of the water soluble paste suspension (B) and the intimate mixture of the two immiscible phases are dispersed in each other and then, with the aid of the colloidal mill, agitated until extremely fine droplets of and encapsulated dye suspension are obtained.

The final composition of the plaque disclosing emulsion then is:

|  | Weight % |
| --- | --- |
| Erythrosine (FD & C Red No. 3) | 0.40 |
| Petrolatum | 9.60 |
| Sodium monofluorophosphate | 0.69 |
| Calcium carbonate | 11.34 |
| Silica | 10.80 |
| Sorbitol (70% solution) | 47.51 |
| Polyethylene glycol | 2.70 |
| Sodium lauryl sulfate | 1.04 |
| Water | 13.50 |
| Sodium carboxymethylcellulose | 1.35 |
| Oil of Peppermint | 0.90 |
| Methylparaben | 0.17 |

The resultant plaque disclosing composition in paste form was applied topically using a cotton applicator in the oral cavity on a clinical trial subject. In this instance, a toothbrush was not used. The subject was instructed to swish the composition around the oral cavity for 1½ minutes and then rinse with water. The oral cavity was then examined and was found to be free of any stains on any portion of the oral cavity.

The same subject was then instructed to apply the plaque disclosing composition in the oral cavity using a toothbrush and brush the teeth for 1½ minutes and then rinse with water. The oral cavity was then clinically examined and the composition/procedure was found to be highly effective in selectively staining plaque formation, rendering the plaque clearly visible to the naked eye. The excess of the composition was easily removed by the rinsing process without staining remaining portions of the oral cavity.

EXAMPLE 2

(A) 40 grams of a mixture of tributyl phosphate and Erythrosine dye (FD&C Red No. 3) in a proportion 2:1 by weight are mixed with a nonionic surfactant, such as Igepal CO 610, and emulsified in 100 grams of 1 percent solution of poly(vinyl methyl ether/maleic anhydride) copolymer half amide, ammonium salt. The resulting emulsion is mixed with 200 grams of a warm (50° C.) 5 percent solution of polyethylene oxide (POLYOX Resin WSR-301). The mixture is then diluted with 200 ml. of water, and stirred and cooled in an ice bath for 30 minutes. It is then treated with 100 grams of a 10 percent solution of ethylene-maleic anhydride copolymer, half methyl ether, which contains 1 ml. of concentrated ammonia. The resulting emulsion is further diluted with 200 ml. of cold water and slowly stirred in an ice bath for 1 hour longer. At this time, 39–40 ml. of 0.3 N hydrochloric acid is added dropwise. The precipitated emulsion is stirred in ice bath for 15 minutes longer. The resultant capsules can be dried and isolated by a variety of techniques. These include spray drying, centrifugation, filtration, etc. In this instance, the capsuled Erythrosine dye was filtered and allowed to dry for 1 hour. After drying, the capsules were weighed and set aside. The weight was 35 grams of which 13.30 grams represented pure Erythrosine dye.

(B) The water soluble phase contained the following:

|  | Weight % |
| --- | --- |
| Stannous fluoride | 0.40 |
| Stannous pyrophosphate | 1.00 |
| Calcium pyrophosphate | 39.00 |
| Glycerin | 10.00 |
| Sorbitol (70% solution) | 16.00 |
| Water | 29.00 |
| Sodium n-lauroyl sarcosinate | 2.00 |
| Cellulose gum | 1.00 |
| Sodium saccharine | 0.20 |
| Oil of wintergreen | 0.90 |
| Sodium benzoate | 0.50 |

After the solidly microencapsulated Erythrosine dye is thoroughly dried (A), 1.50 grams of it is mixed with 98.50 grams of the water soluble paste colloidal suspension (B) and gently but thoroughly stirred until an intimate emulsion of the two immiscible phases is obtained. Mechanical shear devices, such as a colloidal mill, should be avoided lest some of the microencapsulated erythrosine dye may rupture and stain other portions of the oral cavity and non-oral objects when topically applied to the teeth.

The final composition of the plaque disclosing paste prepared according to the microencapsulation method of the present example is:

|  | Weight % |  |
| --- | --- | --- |
| Microencapsulated dye (38% pure Erythrosine) | 1.50 | (Erythrosine 0.57) |
| Stannous fluoride | 0.39 |  |
| Stannous pyrophosphate | 0.99 |  |
| Calcium pyrophosphate | 38.42 |  |
| Glycerin | 9.73 |  |
| Sorbitol (70% solution) | 15.72 |  |
| Water | 28.73 |  |
| Sodium n-lauroyl sarcosinate | 1.99 |  |
| Cellulose gum | 0.99 |  |

|  | Weight % |
| --- | --- |
| Sodium saccharine | 0.19 |
| Oil of Wintergreen | 0.89 |
| Sodium benzoate | 0.46 |

The plaque disclosing composition in paste form was applied topically to the teeth in the oral cavity on a clinical trial subject in the same manner as described above in EXAMPLE 1 with similar results. There was no evidence of staining either of plaque formation or the dentine and the mucous membranes in the oral cavity when the composition was applied with cotton applicator and the subject instructed to swish the composition around the oral cavity for 1½ minutes and then rinse with water. The plaque disclosing composition was completely removed from both the plaque formation and the other portion of the oral cavity, without any sign of discoloration after the initial rinsing.

The result was also similar as in EXAMPLE 1 described above when the clinical subject was instructed to use a toothbrush and brush the teeth for 1½ minutes and then rinse with water. The dye was found to clearly distinguish the plaque formation from the remaining portions of the oral cavity and the excess of the composition was easily removed by rinsing with tap water and the dye which was absorbed by the dental plaque was not removed by this oral rinsing.

EXAMPLE 3

(A) Example 1(A) is repeated except that the water insoluble substance used is mineral oil and to this water insoluble agent Erythrosine dye (FD & C Red No. 3) is added in the same manner as used in Example 1(A) in the same amount, namely 100 grams and 4 grams, respectively.

(B) The water soluble phase in gel form contained the following:

|  | Weight % |
| --- | --- |
| Stannous fluoride | 0.40 |
| Hydrated silica xerogel | 10.00 |
| Hydrated silica aerogel | 11.00 |
| Sorbitol | 67.90 |
| Polyethylene glycol | 5.00 |
| Sodium lauryl sulfate | 1.50 |
| Sodium saccharine | 0.20 |
| Sodium benzoate | 0.50 |
| Cellulose gum | 1.00 |
| Spearmint oil | 1.00 |
| SD alcohol 38B | 1.50 |

Composition (A) and composition (B) are mixed in the same manner and in the same amounts as in Example 1.

The final composition of the plaque disclosing composition in gel form is:

|  | Weight % |
| --- | --- |
| Erythrosine (FD & C Red No. 3) | 0.40 |
| Stannous fluoride | 0.32 |
| Mineral oil | 19.60 |
| Hydrated silica xerogel | 8.00 |
| Hydrated silica aerogel | 8.80 |
| Sorbitol | 54.32 |
| Polyethylene glycol | 4.00 |
| Sodium lauryl sulfate | 1.20 |
| Sodium saccharine | 0.16 |
| Sodium benzoate | 0.40 |
| Cellulose gum | 0.80 |
| Spearmint oil | 0.80 |
| SD alcohol 38B | 1.20 |

The plaque disclosing composition in gel form was applied topically to the teeth in the oral cavity of a clinical trial subject in the same manner as described above in Example 1 with similar results. There was no evidence of staining either plaque formation or other parts of the oral cavity when the composition was applied with cotton applicator. Again the trial subject was instructed to swish the gel composition around the oral cavity for 1½ minutes and rinse with water. There was no residual discoloration of the plaque site or the dentine after the initial rinsing.

The result was again similar as in Example 1 described above when the clinical subject was instructed to use a toothbrush and brush the teeth for 1½ minutes and then rinse with water. There was very evident discoloration of the plaque site after the excess plaque composition was removed by the initial rinsing with water. The dye absorbed by the dental plaque formation tenaciously adhered to the surface of the plaque and was removed by the subsequent brushing.

EXAMPLE 4

(A) To 45 ml. of polyglycol (11-200 Dow Chemical Company) formed by the condensation of glycerol and propylene oxide and having a molecular weight of about 2700, was added 1 gram of FD & C Red No. 3 and 1 gram of FD & C Green No. 3. The solution was then dispersed in 80 grams of 11.1 percent gum arabic and emulsified for 10 minutes, at the end of which time the droplet size varied from about 0.7 to about 5 microns. The dispersion was then added to 80 grams of 11.1 percent solution of pigskin gelatin, the pH of which was adjusted so that the final pH of the mixture was 4.7 to 5. The temperature was kept at 50 to 55 degrees C. While rapidly stirring the mixture, 178 ml. of water was added. The mixture while still being continuously agitated, was then added to a rapidly stirred cold water bath which contained about 2.5 liters and was held at a temperature of 3 to 5 degrees C. The highly swollen coacervate gelled around each oil droplet. A minute amount of antifoaming agent (SS-60-General Electric Company) was added to the chilled bath before the addition of coacervate to eliminate foaming. The mixture was then stirred for approximately 30 minutes to assure separation of each capsule. The capsules were then hardened by the addition of 40 grams of 25 percent of aqueous glutaraldehyde solution and stirred for 3 hours. A 10 percent sodium acetate solution was then added to the suspension while stirring until coagulation occurred. The coagulum was then washed for 3 hours with cold water. The wet coagulum was then drained of excess water and stored, until ready for addition to a water soluble phase (B) as follows:

(B) Example 1(B) is repeated in the same manner and in the same amount using the same ingredients in the same weight percentages.

After the microencapsulated mixture (A) of FD & C Red No. 3 and FD & C Green No. 3 is completely dried, 2.40 grams of it is slowly added to 97.60 grams of the water soluble colloidal suspension (B) and, the two phases are dispersed in each other until an intimate emulsion of the two immiscible phases is obtained. Again, as in Example 2, mechanical shear devices must be avoided.

The final composition of the plaque disclosing paste according to the present example was:

|  | Weight % |  |
| --- | --- | --- |
| Microencapsulated dye (16.66% pure dye) | 2.40 | (FD & C Red 3 = 0.20%) (FD & C Green 3 = 0.20%) |
| Sodium monofluorophosphate | 0.74 |  |
| Calcium carbonate | 12.30 |  |
| Silica | 11.71 |  |
| Sorbitol (70% solution) | 51.53 |  |
| Polyethylene glycol | 2.94 |  |
| Sodium lauryl sulfate | 1.12 |  |
| Water | 14.64 |  |
| Sodium carboxymethylcellulose | 1.46 |  |
| Oil of peppermint | 0.98 |  |
| Methylparaben | 0.19 |  |

The plaque disclosing composition in paste form in accordance with the present invention was applied topically to the teeth in the oral cavity of a clinical trial subject in the same manner as described in Example 1 with similar results. There was no evidence of staining after initial rinsing with water either of plaque formation or the other parts of the oral cavity when the composition was applied with a cotton applicator, but there was a distinct discoloration of the plaque formation when a toothbrush was used, without any undesired discoloration of the other part of the oral cavity. The excess plaque disclosing composition not absorbed by the dental plaque was readily removed in the initial rinsing with water.

EXAMPLE 5

(A) To 45 ml. of a 5 percent solution of azo-bis (isobutyronitrile) in di-n-butyl-phthalate was added 2 grams of Erythrosine dye (FD & C Red No. 3) which was then dispersed into 80 grams of 11.1 percent gum arabic and emulsified until the droplet size varied from about 0.8 to about 6 microns. The dispersion was then added to 80 grams of 11.1 percent solution of gelatin at a temperature of 45 to 50 degrees C. The pH was adjusted to 4.8. While rapidly stirring, 178 ml. of water was added to the mixture. The mixture was then added to 3 liter of cold (5° C.) water in order to gel the coacervate. The capsules were hardened by the addition of 40 grams of a 25 percent solution glutaraldehyde to the suspension and stirred for 3 hours. The suspension was then coagulated by means of sodium acetate after which the coagulum was washed for three hours with cold water. After draining to remove excess water, 50 grams of the coagulum was mixed with 75 ml. of hot water, 10 ml. of 7 percent gelatin solution and two drops of GE SS-60 Anti-foaming Agent. The mixture was dispersed with a Waring Blendor for 20 seconds, then mixed with 0.3 ml. of a 2 percent solution of Duponol dispersing agent, and washed with cold water for 3 hours. The wet coagulum was drained of excess water and stored, until ready for addition to the water soluble phase.

(B) The water soluble phase of the plaque disclosing composition in gel form was prepared in the same manner and in the same amounts using the same ingredients as in Example 3 (B).

After the microencapsulated Erythrosine dye is thoroughly dried, 2.40 grams of it is mixed with 97.60 grams of the water soluble gel colloidal suspension (B) and gently but thoroughly stirred until an intimate emulsion of the two immiscible phases is obtained. Mechanical shear devices, such as a colloidal mill, should be avoided.

The final composition of the plaque disclosing gel prepared according to the microencapsulated example of the present invention is:

|  | Weight % |  |
| --- | --- | --- |
| Microencapsulated dye (16.66% pure dye) | 2.40 | (Erythrosine 0.40%) |
| Stannous fluoride | 0.39 |  |
| Hydrated silica xerogel | 9.76 |  |
| Hydrated silica aerogel | 10.74 |  |
| Sorbitol | 66.28 |  |
| Polyethylene glycol | 4.88 |  |
| Sodium lauryl sulfate | 1.46 |  |
| Sodium saccharine | 0.19 |  |
| Sodium benzoate | 0.48 |  |
| Cellulose gum | 0.98 |  |
| Spearmint oil | 0.98 |  |
| SD alcohol 38B | 1.46 |  |

The plaque disclosing composition in gel form was again applied topically to the teeth of a clinical trial subject in the same manner as described above in all examples with similar results. There was no evidence of staining either plaque formation or other parts of the oral cavity when the composition was applied with a cotton applicator. In a similar manner as in all previous examples, the trial subject was instructed to swish the gel composition in the oral cavity for 1½ minutes and then rinse with water.

However, when the same clinical trial subject was instructed to use a toothbrush and brush the teeth for 1½ minutes and then rinse with water, the dye absorbed by the dental plaque renders the plaque formation distinctly visible to the naked eye distinguishing it from the other parts of the oral cavity and is not removed by the initial rinsing with water as is the excess of the plaque disclosing composition not absorbed by the plaque formation.

EXAMPLE 6

(A) To 80 grams of Petrolatum the following are added: Erythrosine dye (FD & C Red No. 3) 0.40 grams; stannous fluoride 0.40 grams; hydrated silica xerogel 10.00 grams; hydrated silica aerogel 11.00 grams; sorbitol 67.90 grams; sodium lauryl sulfate 1.50 grams; Spearmint oil 1.00 gram; and SD alcohol 38B 1.50 grams. The suspension was run through a colloidal mill three times to insure a homogeneous mixture.

(B) To 20 ml. of water sodium saccharine 0.20 grams, polyethelene glycol 5.00 grams; sodium benzoate 0.10 grams; and cellulose gum 1.00 gram are slowly added with constant stirring until all ingredients are completely dissolved.

80 grams of the previously prepared plaque disclosing dye suspension (A) is added to 20 grams of the water soluble phase (B) and the intimate mixture of the two immiscible phases are dispersed in each other and then, with the aid of the colloidal mill, thoroughly mixed until all components are evenly dispersed and an emulsion of dye suspension with extremely fine droplets is obtained.

The various components are found to be present in the final disclosing composition in the following listed approximate percentages by weight:

|  | Weight % |
| --- | --- |
| Erythrosine dye (FD & C Red No. 3) | 0.40 |
| Stannous fluoride | 0.40 |
| Hydrated silica xerogel | 10.00 |
| Hydrated silica aerogel | 11.00 |
| Sorbitol | 67.90 |
| Sodium lauryl sulfate | 1.50 |
| Spearmint oil | 1.00 |
| SD alcohol 38B | 1.50 |
| Sodium saccharine | 0.20 |
| Polyethylene glycol | 5.00 |
| Sodium benzoate | 0.10 |
| Cellulose gum | 1.00 |

The viscosity of plaque disclosing composition in this example was the same as in the previous examples, however, the higher content of the water insoluble and water immiscible petrolatum (80 percent of the total weight of the composition) contributes to less effective staining of the dental plaque formation on the trial subject when the application is effected either by cotton applicator or by toothbrush. The large amount of the water insoluble and water immiscible substance in proportion to the disclosing dye prevents effective absorption of the dye by the plaque formation when applied to the teeth and is not readily removed by the initial rinsing with water. In addition, the consistency of the gel composition was found to be not quite as acceptable as when the pharmacological and physical aids are dissolved directly in water prior to emulsifying with the water insoluble dye composition.

EXAMPLE 7

Example 1 is repeated except that to 2.25 grams of the water insoluble and water immiscible petrolatum, 2 grams of the Erythrosine dye (FD & C Red No. 3) is added in the same manner to formulate the water insoluble dye phase 1(A).

To 99.55 grams of the water soluble phase of Example 1(B), 0.45 grams of the above dye composition is added and processed in the same manner as in Example 1, i.e., a colloidal mill was used to disperse the dye element into fine droplets. The various components are found to be present in the final disclosing composition in the following listed approximate percentages by weight:

|  | Weight % |  |
| --- | --- | --- |
| Dye composition | 0.45 | (Pure dye 0.40%) |
| Sodium monofluorophosphate | 0.76 |  |
| Calcium carbonate | 12.58 |  |
| Silica | 12.00 |  |
| Sorbitol (70% solution) | 52.60 |  |
| Polyethylene glycol | 3.00 |  |
| Sodium lauryl sulfate | 1.14 |  |
| Water | 14.80 |  |
| Sodium carboxymethylcellulose | 1.48 |  |
| Oil of peppermint | 1.00 |  |
| Methylparaben | 0.19 |  |

There is no appreciable variance in viscosity between the disclosing composition described above and the disclosing compositions of previous examples, however, the lower content of the water insoluble and water immiscible petrolatum (0.45 percent of the total weight of the composition) contributes to a less effective staining of the dental plaque formation on a trial subject when the application is effected either by cotton applicator or by toothbrush. Accordingly, the composition in this example has to be held in contact with the dental plaque for a slightly longer period of time to obtain substantially the same staining effect, and is readily removed by rinsing with water before such staining can be effected.

EXAMPLE 8

Example 3 is repeated except that the water insoluble and water immiscible agent used is lanolin and 20 grams of this water insoluble, dye-containing phase is added in the same manner as used in Example 3 to 80 grams of water soluble phase comprising in approximate weight percent of 0.40% stannous fluoride, 10% hydrated silica xerogel, 11% hydrated silica aerogel, 67.90% sorbiton, 5% polyethylene glycol, 1.50% sodium lauryl sulfate, 0.20% sodium saccharine, 0.50% sodium benzoate, 1% cellulose gum, 1% spearmint oil, and 1.50% SD alcohol 38B.

The various components are found to be present in final disclosing composition in the following listed approximate percentages by weight.

|  | Weight % |
| --- | --- |
| Erythrosine (FD & C Red No. 3) | 0.40 |
| Stannous fluoride | 0.32 |
| Lanolin | 19.60 |
| Hydrated silica xerogel | 8.00 |
| Hydrated silica aerogel | 8.80 |
| Sorbitol | 54.32 |
| Polyethylene glycol | 4.00 |
| Sodium lauryl sulfate | 1.20 |
| Sodium saccharine | 0.16 |
| Sodium benzoate | 0.40 |
| Cellulose gum | 0.80 |
| Spearmint oil | 0.80 |
| SD alcohol 38B | 1.20 |

The plaque disclosing composition described above is found to be very effective in selectively staining the plaque formations in the oral cavity through topical application to the teeth. Initially, the composition is applied to the teeth of a selected clinical trial subject by means of a cotton applicator and the subject is instructed to swish the composition in the mouth and around the teeth for 1½ minutes and then rinse with water. Since there is no dissolution of the dye element to affect the plaque formation, the plaque disclosing composition was quickly and completely removed from the site of plaque formation and the remaining portion of the oral cavity without any distinguishing sign of discoloration of either.

Almost immediately thereafter, the composition is applied to the teeth of the same clinical trial subject by means of a toothbrush and the subject is instructed to brush the teeth thoroughly for 1½ minutes and then rinse with water. The dye was found to clearly distinguish the site of plaque formation from the remaining portion of the oral cavity. During the rinsing process, the water insoluble substance tenaciously adheres to the plaque formation and is not removed until subsequent brushing but the excess composition is readily removed by this oral rinsing.

The same clinical trial subject is used for both application of the plaque composition by means of cotton applicator and application by toothbrush, to more dramatically illustrate the effectiveness and efficiency of the plaque disclosing composition of the present invention under similar conditions.

EXAMPLE 9

A set of plaque disclosing compositions were made in which the water soluble phase containing the pharmaceutical and physical aids contained the same ingredients and in the same amount as in Example 3 (B) and in which the dye disclosing element Erythrosine (FD & C Red No. 3) in the amount of 0.40 percent was suspended in a plurality of emulsifying and thickening agents in amounts to produce viscosities from about 50,000 to about 120,000 centipoise.

| Disclosing Composition | Emulsifying and Thickening (Gelling) Agent |
| --- | --- |
| A | White wax |
| B | Canada balsam |
| C | Hydroxyethyl cellulose |
| D | Sodium carboxymethylcellulose |
| E | Silica aerogel |
| F | Tragacanth |
| G | Paraffin |
| H | Cottonseed oil |

The above set of plaque disclosing compositions were prepared in the same manner and in the same amounts as in Example 1.

A sample of each plaque disclosing composition was used on selected clinical trial subjects of similar oral manifestations of plaque accumulation on their teeth and presenting the following characteristics:
1. were not undergoing orthodontic treatment.
2. did not wear partial dentures.
3. hand no more than six teeth missing on either arch.
4. no clinically detectable periodontal involvement.
5. had prophylaxis at least one month prior to the study but not more than six months.
6. were not undergoing extensive restorative treatment during the study.

The plaque disclosing composition was applied to the assigned participant's teeth by means of cotton applicator and the participant was instructed to swish the composition around the teeth for 1½ minutes and then rinse with water. Teeth were examined then for staining of the plaque formation and other portions of the oral cavity before the participant was instructed to use a toothbrush for application of the assigned plaque composition to the teeth and again brush for about 1½ minutes before rinsing with water. Teeth were then again examined for clinical manifestations of staining of plaque formations and discolorations of other parts of the oral cavity and recorded. The results were as follows:

| Disclosing Composition | Staining | | | |
| --- | --- | --- | --- | --- |
| | Cotton Applicator | | Toothbrush | |
| | Plaque Formation | Other Parts | Plaque Formation | Other Parts |
| A | No staining | No staining | Staining | No staining |
| B | No staining | No staining | Staining | No staining |
| C | Staining | Staining | Staining | Staining |
| D | Staining | Staining | Staining | Staining |
| E | Staining | Staining | Staining | Staining |
| F | Staining | Staining | Staining | Staining |
| G | No staining | No staining | Staining | No staining |
| H | No staining | No staining | Staining | No staining |

The above table indicates that disclosing compositions C, D, E and F being water soluble emulsifying and thickening (gelling) agents are not selectively staining plaque formations in the oral cavity when applied either by means of cotton applicator or toothbrush even in a high viscosity range of 50,000 to 120,000 centipoise. Disclosing compositions A, B, G, and H, being water insoluble, are highly selective in staining plaque formation in the oral cavity only when a toothbrush was used to apply the composition on the teeth of each participant. Furthermore, the water insolubility of the dye dispersion medium is far more important in the selective staining of the plaque formation than is the viscosity of the said dye dispersion medium which, in aqueous environment, would partially dissolve together with the dye element resulting in indiscriminate discoloration of the entire oral cavity as was found in samples C, D, E, and F.

Thus, there has been described a unique and novel dental disclosing composition comprising dye dispersion rather than dye solution which is easily applied to the teeth in a human oral cavity for selective staining of any plaque formation therein and which does not undesirably stain other portions of the oral cavity, and thereby fulfills all the objects and advantages sought for evaluation and motivation in the tooth brushing practices of the user. It should be understood that changes and modifications including the substitution, elimination or addition of various components can be made in the subject disclosing compositions, or the method of making such compositions, or the method of using such compositions, without departing from the nature and principle of the invention. Therefore, all such changes and modifications which do not depart from the nature and principle of the invention are deemed to be covered by the invention which is limited only by the claims.

The invention provides a method and process for making a plaque disclosing composition for topical application in the oral cavity for selectively staining the sites of dental plaque formations comprising a continuous phase of water soluble, water miscible, hydrophilic colloid comprising pharmacologically and physiologically harmless pharmacological and physical aids and uniformly dispersed throughout said continuous phase and a discontinuous phase of water insoluble water immiscible, hydrophobic emulsion of pharmacologically and phsiologically harmless plaque staining dye elements, the dye elements being rendered substantially less water soluble when effectively applied in the oral cavity permitting for selective absorption of the said pharmacologically and physiologically harmless plaque staining dye elements by the sites of dental plaque formations without appreciably staining other portions of the oral cavity and non-oral objects, the excess of the plaque disclosing composition being readily removed by rinsing with water and other rinsing solutions.

The invention also provides a method and process for making a plaque disclosing composition for topical application in the oral cavity for selectively staining the sites of dental plaque formations comprising a continuous phase of water soluble, water miscible, hydrophilic colloid comprising pharmacologically and physiologically harmless pharmacological and physical aids selected from a class consisting of sweeteners, flavoring agents, humectants, abrasives, thickeners and emulsifiers, fluoride compounds, preservatives, surface active agents, alcohols, and water and uniformly dispersed throughout said continuous phase, and a discontinuous phase of water insoluble, water immiscible, hydrophobic emulsion of pharmacologically and physiologically harmless plaque staining dye elements comprise members of a group consisting of substances which are dyes, pigments and other substances made by a process of synthesis or similar artifices, or extracted, isolated, or otherwise derived, with or without intermediate or final change of identity, from a vegetable, animal, mineral, or other source that, when added or applied to plaque formation or any other substance or surface, is capable alone or through reaction with other substances, of imparting a color thereto, the dye element being rendered substantially less water soluble when effectively applied in the oral cavity permitting for selective absorption of the said pharmacologically and physiologically harmless plaque staining dye elements by the sites of dental plaque formations without appreciable staining other portions of the oral cavity and non-oral objects, the excess of the plaque disclosing composition being readily removed by rinsing with water and other rinsing solutions.

The invention further provides a method and process for making a plaque disclosing composition for topical application in the oral cavity for selectively staining the sites of dental plaque formations comprising a continuous phase of water soluble, water miscible, hydrophilic colloid comprising pharmacologically and physiologically harmless pharmacological and physical aids and uniformly dispersed throughout said continuous phase and a discontinuous phase of emulsified plaque disclosing dye elements each comprising a core or protective covering comprising a soft semi-solid or soft solid water insoluble, water immiscible, pressure rupturable, hydrophobic fine droplets of the emulsified plaque staining dye elements and a soft semi-solid or soft solid water insoluble, water immiscible, pressure rupturable capsule of the emulsified plaque staining dye elements, the dye elements being rendered substantially less water soluble when effectively applied in the oral cavity permitting for selective absorption by any plaque sites in the human oral cavity of the plaque disclosing dye elements when pressure is applied on the said plaque disclosing compositions rupturing the emulsified dye containing droplets or capsules thereby liberating the water soluble dye elements to affect the selective staining of the immediately positioned plaque formation with appreciably staining other portions of the oral cavity and non-oral objects, the excess plaque disclosing composition being readily removed by rinsing with water and other rinsing solutions.

The invention further provides a process and method for making a plaque disclosing composition wherein the pharmacologically and physiologically harmless plaque staining dye elements are selected from FD & C Red No. 3, FD & C Yellow No. 5, FD & C Yellow No. 6, FD & C Green No. 3, FD & C Blue No. 1, FD & C Blue No. 2, and FD & C Green No. 2 and mixtures thereof.

The invention further provides a process and method for making a plaque disclosing composition wherein the pharmacologically and physiologically harmless pharmacological and physical aids are being added in non-toxic amounts within the following range percent by weight based on the total weight of the composition: (a) sweeteners, 0.05-5.00%; (b) flavoring agents, 0.05-25%; (c) humectants, 2.0-65%; (d) abrasives, 1.0-65%; (e) thickeners and emulsifiers, 0.05-10%; (f) fluoride compounds, 0.10-5%; (g) preservatives, 0.05-5%; (h) surface active agents, 0.05-5%; (i) alcohols, 0.10-20%, and (j) water, 0.0-50% and mixtures thereof and wherein the pharmacologically and physiologically harmless plaque staining dye elements are present in the operative range in the amount from about 0.05 percent to about 25 percent by weight with respect to the weight of the total composition and preferably present from about 0.1 percent to about 10 percent of the total weight of the composition.

The invention also provides a method and process for making a plaque disclosing composition for topical application in the oral cavity wherein the continuous phase of water soluble, water miscible, hydrophilic colloid is present in the operative range in an amount from about 0.5 percent to about 75 percent by weight with respect to the weight of total composition and preferably present in an operative range of about 5 percent to about 65 percent by weight with respect to the total weight of the composition and wherein the discontinuous phase of water insoluble, water immiscible hydrophobic emulsion is present in an operative range in an amount from about 0.1 percent to about 50 percent by weight with respect to the total weight of the composition and preferably present in an operative range of about 1 percent to about 35 percent by weight with respect to the total weight of the composition.

The invention further provides a method and process for making a plaque disclosing composition wherein the water soluble, water miscible, hydrophilic phase is not less than twice the amount of the water insoluble, water immiscible hydrophobic emulsion phase.

The invention also provides a method and process for making a plaque disclosing composition wherein the composition is paste or gel.

The invention further provides a method and process for making a plaque disclosing composition wherein the pharmacologically and physiologically harmless dye elements are encapsulated FD & C Red No. 3 and FD & C Green No. 3 in equal amounts.

The invention further provides a method and process for making a plaque disclosing composition wherein the pharmacologically and physiologically harmless dye element is encapsulated FD & C Red No. 3.

The invention further provides a method and process for making a plaque disclosing composition for topical application in the oral cavity for selective staining of sites of dental plaque formations comprising a continuous phase of water soluble, water miscible, hydrophilic colloid comprising pharmacologically and physiologically harmless thickening and emulsifying agents dissolved in water and uniformly dispersed throughout said continuous phase and a discontinuous phase of water insoluble, water immiscible, hydrophobic emulsion comprising pharmacologically and physiologically harmless plaque staining dye elements in intimate mixing with equally pharmacologically and physiologically harmless pharmacological and physical aids, the dye element being rendered substantially less water soluble when effectively applied in the oral cavity permitting for selective absorption of the said pharmacologically and physiologically harmless plaque staining dye elements by the sites of dental plaque formations without appreciable staining of other portions of the oral cavity and non-oral objects, the excess of the plaque disclosing composition being readily removed by rinsing with water and other rinsing solutions.

The invention further provides a method and process for making a plaque disclosing composition for topical application in the oral cavity wherein the discontinuous phase of water insoluble, water immiscible, hydrophobic emulsion is selected from the class consisting of lipids, alkones, fixed oils, and resins.

The invention further provides a method and process for making a plaque disclosing composition for topical application in the oral cavity wherein the water insoluble, water immiscible, hydrophobic emulsion is petrolatum.

The invention further provides a method and process for making a plaque disclosing composition for topical application in the oral cavity for selectively staining the sites of dental plaque formations, said method and process comprising adding to a selected dispersion medium a selected dye in an amount sufficient to provide a desirable staining quality, dispersing the said dye solution in an aqueous solution of an emulsifying agent forming fine droplets of a dye element emulsion, dispersing the said dye emulsion in an aqueous solution of gelatin, adjusting the pH of the solution from about 4 to about 8, rapidly stirring the mixture and adding warm water, adding the warm mixture in cold water with continuous stirring, forming a gelled coarcervate around each droplet, adding a hardening solution and continued stirring for three hours to insure separation of each droplet, adding a solution of sodium acetate while stirring until coagulation occurred, washing the coagulum with cold water, drained of excess water and dried, adding a desired amount of so prepared dye emulsion to a predetermined amount of water soluble, water miscible, hydrophilic colloidal dispersion dissolved therein pharmacological and physical aids in selected amounts, mechanically mixing the two immiscible phases into an intimate emulsion in such a way in which the water insoluble phase containing the dye elements is dispersed in the form of fine and separate droplets in the water soluble phase, the final composition being rendered substantially less water soluble when effectively applied to the oral cavity with a hard object, such as a toothbrush, rupturing the dye containing droplets thereby liberating the water soluble dye elements to effect the selective staining of the plaque formation without appreciably staining other portions of the oral cavity and non-oral objects, the excess plaque disclosing solution being readily removed by rinsing with water and other rinsing solutions; and when effectively applied to the oral cavity with an object of a hardness insufficient to rupture the dye containing droplets does not appreciably stain either the plaque formation or the other portions of the oral cavity and non-oral object, the entire plaque disclosing composition so applied being readily removed by the initial rinsing with water and other rinsing solutions.

The invention further provides a method for visualizing plaque formation in the oral cavity for use in the self evaluation and motivation of oral hygiene practices, whereby any plaque present in the oral cavity is readily visible to the naked eye.

In view of the above disclosure, it will be noted that the several objectives of the invention are achieved and other advantageous results obtained, therefore, what I desire to claim and secure by Letters Patent is:

1. A diagnostic plaque disclosing dentifrice composition for topical application to the teeth comprising a continuous water soluble phase, and a discontinuous water insoluble phase dispersed in said water soluble phase, said water insoluble phase comprising selectively rupturable dye elements, with a dental plaque disclosing substance dispersed in said rupturable dye elements, whereby said dental plaque disclosing substance may be topically applied to said teeth by rupturing said selectively rupturable dye elements.

2. The invention as defined in claim 1 wherein said selectively rupturable dye elements additionally comprise a water insoluble substance, said water insoluble substance having a high affinity for adsorption by dental plaque.

3. The invention as defined in claim 1 wherein said composition is formed as a homogeneous paste.

4. The invention as defined in claim 1 wherein said composition is formed as a homogeneous gel.

5. The invention as defined in claim 2 wherein said water insoluble substance is a semi-solid, said semi-solid microencapsulating said plaque disclosing substance.

6. The invention as defined in claim 1 wherein said water soluble phase forms at least two-thirds, by weight, of said composition.

7. The invention as defined in claim 1 wherein said water soluble phase comprises water and a member selected from the group consisting of flavorings, non-staining colors, sweeteners, alcohols, abrasives, humectants, thickening and emulsifying agents, fluorides, and preservatives.

8. The invention as defined in claim 1 wherein said water insoluble substance is a lipid.

9. The invention as defined in claim 1 wherein said water insoluble substance is an alkane series hydrocarbon selected from the group consisting of mineral oil, petrolatum, white petrolatum, and paraffin.

10. The invention as defined in claim 1 wherein said water insoluble substance is a fixed oil selected from the group consisting of cottonseed oil, olive oil, and neutral esters of organic acid with glycerine.

11. The invention as defined in claim 1 wherein said water insoluble substance is a substance derived from plant origin selected from the group consisting of resins derived from plant origin, Canada balsam, Peruvian balsam, copal, mastic, rosin, and benzoin.

12. The invention as defined in claim 1 whrein said dental plaque disclosing substance is a member selected from the group consisting of FD & C Red No. 3, FD & C Yellow No. 5, FD & C Yellow No. 6, FD & C Green No. 3, FD & C Blue No. 1, and FD & C Blue No. 2.

13. A method for visualizing plaque formation in the oral cavity and for self evaluation and motivation of oral hygiene practices without excessively staining non-dental portions of the oral cavity, comprising the steps of:
(a) applying a portion of the composition of claim 1 to the teeth so that said rupturable elements are adsorbed by plaque formations;
(b) brushing the composition on the teeth so as to rupture said rupturable elements and disclose said plaque formations with said plaque disclosing substance but without appreciably staining other parts of the oral cavity; and (c) further brushing the teeth so as to remove the plaque disclosed by said disclosing substance.

14. The invention as defined in claim 5 wherein said semi-solid comprises petrolatum.

15. The invention as defined in claim 1 wherein said water soluble phase comprises about 0.5 to 75% water, and said water soluble phase additionally comprises about 1 to 65% abrasives, about 0.05 to 5% thickners and emulsifiers, and about 0.05 to 5% surface active agents.

16. The invention as defined in claim 1 wherein said water soluble phase comprises a conventional toothpaste.

17. The invention as defined in claim 2 wherein said dental plaque disclosing substance is dispersed in said selectively rupturable dye elements by suspending said dental plaque disclosing substance in said water insoluble substance.

18. The invention as defined in claim 17 wherein said water insoluble substance comprises petrolatum.

19. The invention according to claim 1 wherein said selectively rupturable dye elements comprise droplets dispersed in said water soluble phase.

20. A process for making a plaque disclosing dentifrice composition, said composition comprising semi-solid capsules of dye, said process comprising the steps of:
    forming selectively rupturable dye elements by encapsulating a plaque disclosing dye in a water insoluble substance, and
    incorporating said selectively rupturable elements in a dentifrice composition.

21. The process according to claim 20 wherein said forming step comprises the encapsulation of FD & C Red No. 3 dye in petrolatum by first suspending said dye in said petrolatum, and then running said suspension through a colloidal mill a sufficient number of times to insure homongeneity of said suspension.

* * * * *

UNITED STATES PATENT AND TRADEMARK OFFICE
CERTIFICATE OF CORRECTION

PATENT NO. : 4,348,378
DATED : November 8, 1982
INVENTOR(S) : Carl M. Kosti

It is certified that error appears in the above—identified patent and that said Letters Patent is hereby corrected as shown below:

Col. 6, line 37, delete "V", insert --v--.

Col. 6, line 53, after "alkane", delete --oil--.

Col. 7, line 1, delete "soluble", insert --insoluble--.

Col. 8, line 37, delete "proprotions", insert --proportions--.

Col. 9, line 7, delete "pottasium", insert --potassium--.

Col. 11, line 33, after "of", insert --emulsified--.

Col. 20, line 57, delete "phsiologically", insert --physiologically--.

Col. 23, line 14, delete "alkones", insert --alkanes--.

Col. 24, line 51, delete "whrein", insert --wherein--.

Signed and Sealed this

First Day of February 1983

[SEAL]

Attest:

GERALD J. MOSSINGHOFF

Attesting Officer

Commissioner of Patents and Trademarks